United States Patent [19]

Partanen et al.

[11] Patent Number: 5,420,012

[45] Date of Patent: May 30, 1995

[54] METHOD FOR THE DETECTION OF REACTIVE CONDITIONS

[75] Inventors: Paul Partanen; Sari Ylatupa; Raili Paasivuo; Ismo Virtanen, all of Helsinki, Finland

[73] Assignee: Locus Genex Oy, Helsinki, Finland

[21] Appl. No.: 965,928

[22] Filed: Oct. 23, 1992

Related U.S. Application Data

[63] Continuation-in-part of Ser. No. 461,710, Jan. 8, 1990, abandoned.

[30] Foreign Application Priority Data

May 8, 1989 [FI] Finland .................................. 892197

[51] Int. Cl.$^6$ ........................................... G01N 33/574
[52] U.S. Cl. ................................ 435/7.23; 435/7.92; 435/7.93; 436/518; 436/531; 436/813; 436/815
[58] Field of Search ............... 436/518, 811, 813, 815, 436/530, 531; 435/7.1, 7.93, 7.94, 7.92, 7.23

[56] References Cited

U.S. PATENT DOCUMENTS 4,980,279 12/1990 Peters et al. .................... 436/547 X

OTHER PUBLICATIONS

Laitinen et al., "Distribution of Extra-Domain (ED-)-Containing Form of Cellular Fibronectin in Human Solid Tumors", Int. Congr. Acad. Pathology, Dublin 1988, Abstract. 144.
Vartio et al., "Differential Expression of the ED Sequence-Containing Form of Cellular Fibronectin in Embryonic and Adult Human Tissues", *J. Of Cell Science,* vol. 88, pp. 419–439 (1987).
Ylätupa et al., Journal of Immunological Methods, 163 (1993) 41–47; 1993 Elsevier Science Publishers B.V. "Competitive Enzyme Immunoassay for Quantification of the Cellular Form of Fibronectin (EDAcFN) In Blood Samples" pp. 41–47.
Walle et al., Scand J. Immunol. 31, 535–540, 1990, "Cellular Fibronectin in Rheumatoid Synovium and Synovial Fluid: a Possible Factor Contributing to Lymphocytic Infiltration".
Linnala et al., Federation Of European Biochemical Societies, Feb., 1992, vol. 317, No. 1,2, pp. 74–78, "Human Amnion Epithelial Cells Assemble Tenascins and Three Fibronectin Isoforms in the Extracellular Matrix".
Preprint: "Cellular Fibronectin (EDAcFN) Concentration in Various Body Fluids", by Ylatupa et al.
Preprint: "Cellular Fibronectin in Serum and Plasma. A Potential New Tumor Marker?", by Ylatupa et al.

*Primary Examiner*—Esther M. Kepplinger
*Assistant Examiner*—Susan C. Wolski

[57] ABSTRACT

The invention relates to diagnosis of reactive conditions, such as malignant tumors. According to the invention, the amount of cellular fibronectin in a body fluid is determined, and an elevated amount is used as a marker for a reactive condition. The method is especially suitable for the diagnosis of carcinomas, such as colon carcinoma.

4 Claims, 5 Drawing Sheets

METHOD FOR THE DETECTION OF REACTIVE CONDITIONS

CROSS-REFERENCE TO RELATED APPLICATIONS

This application is a continuation-in-part of application Ser. No. 07/461,710 filed on Jan. 8, 1990, now abandoned.

TECHNICAL FIELD OF THE INVENTION

This invention relates to diagnosis of reactive conditions such as malignant tumors by detecting a marker in body fluid.

BACKGROUND OF THE INVENTION

The diagnosis of, e.g., malignant tumors is conventionally based on tissue investigation, such as biopsy.

The general object of the present invention is to provide a diagnosis method based on a general marker to be found in body fluids.

GENERAL DESCRIPTION OF THE INVENTION

We have now discovered that cellular fibronectin or its specific extra domain (ED) sequence in human or animal body fluids (e.g. blood, urine, or bronchoalveolar liquid, BAL) can be used as a marker for reactive conditions or stages, such as malignant tumors or autoimmune diseases wherein anti-mitochondrion antibodies are raised.

Cellular fibronectin or its extra domain sequence can be detected by using immunological methods with specific antibodies to the extra domain sequence.

The method is especially suitable for the detection of carcinomas.

The clinical value of the determination of increased ED containing fibronectin during different reactive conditions in body fluids is significant, because there are no other good general markers for these stages available.

DETAILED DESCRIPTION OF THE INVENTION

Fibronectins are high molecular weight adhesive glycoproteins that have variable primary structures. Fibronectins can be divided into two major groups: soluble plasma fibronectins (pFN), and cellular fibronectins (cFN) which are insoluble tissue proteins. Cellular fibronectin differs from plasma fibronectin in having the so called extra domain (ED) sequence in the molecule. In plasma the soluble fibronectin is an important protein component and several results have shown that the plasma form of the fibronectin molecule is primarily produced by hepatocytes (Tamkun and Hynes, J. Biol. Chem., 1983, 256:4641), but can be retained also in extracellular matrix of cells both in vivo and in vitro. The cellular form of fibronectin is produced locally. However, plasma also contains small quantities of the cellular form.

Many recent results have shown that fibronectins form a large isomorphic protein family, the members of which differ from each other only little (Kornblight and Gutman, Biol. Rev. 63:465, 1988; Ruoslahti, Ann. Rev. Biochem. 57:375, 1988). Molecular biology results have also shown that the structure of fibronectin, depending on cells producing it, is different with respect to the extra domains (short sequences of amino acids) produced by differential splicing of messenger-RNA from a single gene. Such known sequences are extra domain A (EDA) and extra domain B (EDB) and the so called IIICS connecting sequence. Many results point out to the fact that these domains are differently produced at the cellular level in cellular fibronectins (e.g. Tamkun et al., PNAS 81:5140, 1984). EDA-sequence containing fibronectin is largely confined to the endothelium of larger blood vessels, whereas this form of the fibronectin molecule is lacking in adult tissues.

Figure 4:
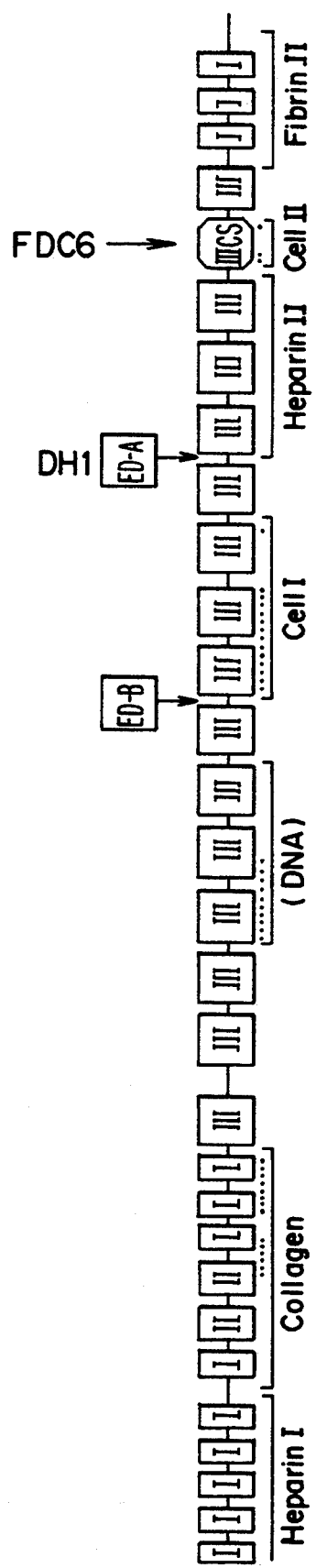

Matsuura et al. (J. Biol. Chem. 1988, 263:3314) have established a monoclonal antibody FDC-6, which reacts specifically with the above mentioned IIICS connecting sequence. FIG. 4 shows a structural map of fibronectin showing repeating homologous units. Fibronectin is composed of three main homologies that are repeated several times in the molecule. The repeats have been marked I, II and III. Marked are also areas in which differential splicing can produce or remove type III modules, ED-A and ED-B or portions of IIICS region. The labels at the bottom of the figure indicate functional binding domains of fibronectin, binding to heparin, fibrin, collagens, DNA or cells. The binding domains of Mab DH1 and FDC6 have been marked.

Monoclonal antibodies used in this invention, reacting specifically with EDA containing fibronectins can be prepared by using conventional methods (Vartio, T. et al., Differential expression of the ED sequence-containing form of cellular fibronectin in embryonic and adult human tissues, J. Cell Sci. 88:419–430 (1987); Virtanen, I. et al., Differential expression of the extra domain-containing form of cellular fibronectin in human placentas at different stages of maturation, Histochemistry 90:25–30 (1988), which papers are incorporated as references herein). By using a monoclonal antibody, it has been shown that in adult tissues EDA containing fibronectin is only present in larger endothelia and smooth muscle cells but it is present in the stromal tissues of all carcinomas (Laitinen, L. et al., Distribution of extra domain (ED)-containing form of cellular fibronectin in human solid tumors, Int. Congr. Acad. Pathology, Dublin 1988, Abstr. 144).

Monoclonal or polyclonal antibodies to EDA or its synthetic parts, i.e. synthetic peptides of the EDA sequence, the whole EDA or shorter or longer parts of it, can be used to detect EDA or EDA containing polypeptides in body fluids. Any body fluid containing cFN, e.g. blood (serum or plasma), BAL fluid (bronchoalveolar liquid), or urine can be used.

Any suitable immunological methods can be used to detect the EDA. Such methods are, for example, enzyme immuno assays (EIA), enzyme linked immunosorbent assays (ELISA), radio immuno assays (RIA), fluorescence immuno assays (FIA), luminescence immuno assay (LIA), latex or other agglutination methods, particle counting immuno assays (PCIA), immunoblottings, immunoprecitation methods, or methods utilizing different kinds of biosensors.

In the determination especially the ratio of EDA containing cellular fibronectin to total fibronectin seems to be valuable. However, the measurement of the concentration of just the EDA containing fibronectin only is enough to demonstrate the reactive condition. The concentration of total fibronectin in human plasma is about 300(+) μg/ml, while the concentration of cellular fibronectin in normal human plasma is about 3(+) μg/ml.

Experimental

EXAMPLE 1

A solid phase EIA method was used to detect EDA containing cellular fibronectin in human sera, plasma or BAL (bronchoalveolar liquid).

Monoclonal antibodies 52 DH1 and 52 BF12 were used, (see Vartio et al., ibid.). 52 DH1 reacts only with the extra domain A of cellular fibronectin and 52 BF12 reacts with fibronectin. 53 BF12 (BF) and 52 DH1 (DH) were made by immunizing Balb/c mice with fibronectin produced by A8387 cells. Three days after the third immunization the spleens were removed, the cells fused with myeloma cells (NS-1) and hybrid selection was initiated 3 days later by standard techniques (Kohler & Milstein, Eur. J. Immun., 1976, 6:511–519; see Virtanen et al., Ann N.Y. Acad. Sci., 1985, 455:635–648). Hybridomas were screened by using a solid-phase immunoassay with pFn and cFn as well as immunofluorescence microscopy with cultured human fibroblasts. Cloning of the hybridomas was done manually by collecting single cells with a micropipette and the clones were initially propagated by using mouse peritoneal macrophages as feeder cells. The BF and DH antibodies were IgG$_1$ type, as determined by radial immunodiffusion by using a commercial kit (Miles, Elkhart, Ind.) according to the instructions of the manufacturer. Ascites fluid production in Balb/c mice with the hybridoma cells was initiated by standard techniques (Kohler & Milstein, 1976; Virtanen et al., 1985). Affinity purified immunoglobulins (G-protein Sepharose, Pharmacia-LKB Biotechnology, Uppsala, Sweden) were used to develop the solid phase enzyme immunoassay.

The solid phase enzyme immunoassay was sandwich type, where the 52 DH1 affinity purified immunoglobulins were used to coat the solid phase support (MaxiSorp F8 microwells, Nunc, Kamstrup, Denmark) and the 52 BF12 affinity purified immunoglobulins conjugated to horseradish peroxidase used as detection system, or vice versa. The conjugated polyclonal antibody to fibronectin can naturally be used instead of labelled monoclonal (BF12), or vice versa.

It was found beneficial to dilute the samples before incubation. Preferable dilution was 150–1:100, whereby relatively small cFN concentrations (0.02 μg/ml) could still be detected.

The samples were incubated for 1 hour at 37° C. (except in substrate incubation 30 min at room temperature). The wash solution was 0.02M PBS pH 7.0+0.1% Tween 20. The wells were washed 5 times with 200 μl of wash solution.

Colon carcinoma and autoimmune diseased human sera were used to detect elevated levels of EDA containing fibronectin. Healthy blood donor sera (from Finnish Red Cross Transfusion Center, Helsinki, Finland) were used to evaluate the average concentration of EDA containing fibronectin in human sera.

In patients with colon carcinoma it was possible to demonstrate elevated concentrations of EDA containing fibronectin in blood circulation. 20 out of the 20 studied colon carcinoma patients sera were positive for EDA containing fibronectin showing at least twofold increase of the concentration in their sera compared to healthy blood donors. In most cases studied autoimmune patients' sera were negative for cFN, but for instance the AMA patient's serum (with elevated amounts of antimitochondrial antibodies) was showing high concentration of EDA containing fibronectin.

Figure 1:
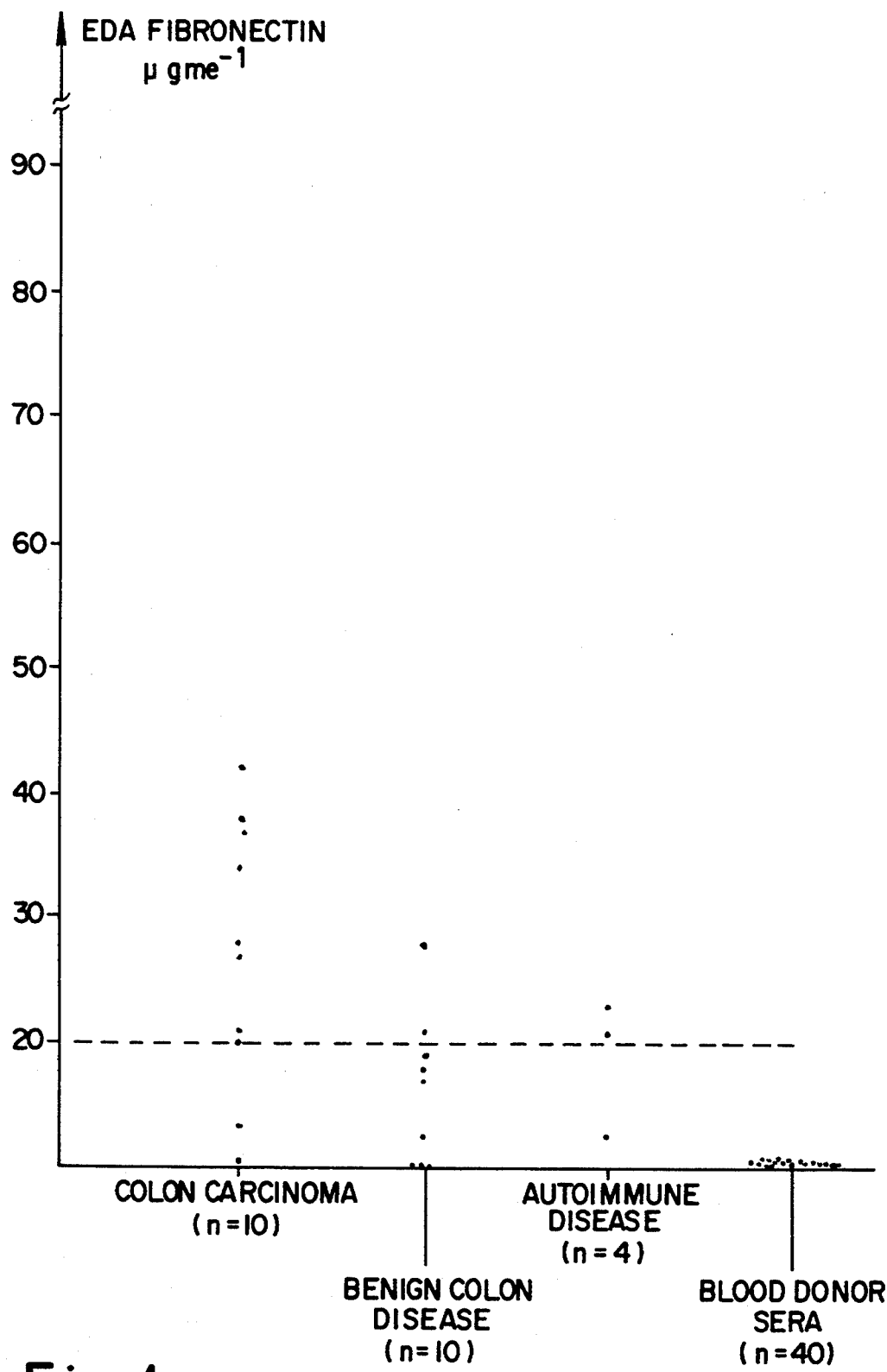
FIG. 1 shows the levels of EDA-containing fibronectin in blood of patients with colon carcinoma, benign colon disease, autoimmune disease, and normal blood donors according to Example 1.

Results are illustrated in the enclosed FIG. 1.

EXAMPLE 2

Cellular fibronectin content of sera and plasma from healthy blood donors and patients having malignant tumors or benign conditions.

Isolation of FNs

FN from the sera or human plasma (Finnish Blood Transfusion Service, Helsinki, Finland) was isolated by affinity chromatography on gelatin-Sepharose 4B (Pharmacia, Uppsala, Sweden), as described (Engwall and Ruoslahti, 1977, Int. J. Cancer, 20:1–5). Cellular fibronectin, produced by A 8387 fibrosarcoma cells (Department of Anatomy, University of Helsinki), was isolated by using the same method from collected spent growth medium of the cells, seeded after trypsinization in serum-free medium to avoid co-purification of serum FN.

Human sera and plasma

Sera and plasma from healthy blood donors were obtained from Finnish Blood Transfusion Service, (Helsinki, Finland). Malignant tumors and benign conditions sera and plasma were obtained from the 4th Department of Surgery, Helsinki University Central Hospital (Helsinki, Finland).

Monoclonal antibodies

The monoclonal antibody 52HD1, reacting only with the extra domain A (EDA) of cellular fibronectin and the other Mab 52BF12 reacting with fibronectin, has been raised and characterized recently (Vartio et al., 1987, ibid.). Affinity purified immunoglobulins (G-protein Sepharose, Pharmacia-LKB Biotechnology, Uppsala, Sweden) were used to develop the solid phase enzyme immunoassay. Immunoglobulins were IgG1 class.

Conjugation of antibodies to horseradish peroxidase 2 mg of horseradish peroxidase (POD) (Boehringer Mannheim, Darmstadt, Germany) was dissolved in 0.5 ml of distilled water. 0.1 ml of 0.2M NaIO$_4$ solution was added and stirred for 20 minutes at room temperature. The POD-aldehyde solution was dialyzed overnight against 1 mM sodium acetate buffer pH 4.5. The pH of the dialyzed solution was adjusted to 9.5 with 0.2M carbonate/bicarbonate buffer pH 9.5. 4 mg of IgG, dissolved in 0.5 ml of 10 mM carbonate/bicarbonate buffer pH 9.5 was added and the mixture was stirred for two hours at room temperature. 0.005 ml of NaBH$_4$ solution (4 mg/ml) was added and the mixture was allowed to stand for two hours at +4° C. with occasional shaking. The solution was dialyzed against 0.01M phosphate buffered saline, pH 7.4. Bovine serum albumin and sodium azide were added to the conjugate to concentrations of 5 mg/ml and 0.1% (w/v), respectively.

Competitive Enzyme Immunoassay 96-well microtitration plates (High binding, Biohit, Helsinki, Finland) coated overnight with 100 μl of purified cellular fibronectin were washed four times with a 0.02M phosphate buffered saline pH 7.0, 0.1% Tween 20 prior to use. The assay was started by incubating separately 50 μl of the sera and plasma samples or standards with 50 μl of the peroxidase conjugated 52DH1 in a separate non-coated plate. After one hours incubation the samples were transferred to the coated plate and incubated for one hour. The unbound material was removed by washing 4 times with the above washing buffer. The bound enzyme activity was visualized by addition of 100 μl of substrate solution containing hydrogen peroxide and tetramethyl benzidine (TMB) (Merck, Darmstadt, Germany). The color formation was allowed to proceed for 30 minutes, after which 100 μl of 2N $H_2SO_4$ was added. Optical density was measured in an Anthos microtitre plate reader (Anthos Microsysteme, Köln, Germany) at 450 nm.

Electrophoresis and Immunoblotting

Sodium dodecyl sulphate-polyacrylamide gel electrophoresis (SDS-PAGE); (Laemmli, 1970, Nature, (London) 227:680–686) was performed by using 6,5% vertical slab gel under reducing conditions. After electrophoresis, the gels were either protein stained (Fairbanks et al., 1971, Biochemistry, 10:2606–2617) or immunoblotted. Immunoblotting (Towbin et al., 1979, Proc. Natl Acad. Sci. USA, 76:4350–4354) was performed by transferring SDS-PAGE-separated polypeptides onto nitrocellulose sheets (Hoefer Scientific Instruments, San Francisco, Calif., USA). Immunoreactions were detected by peroxide-coupled Mabs 52DH1 or 52BF12.

Results

Enzyme immunoassays

Figure 2:
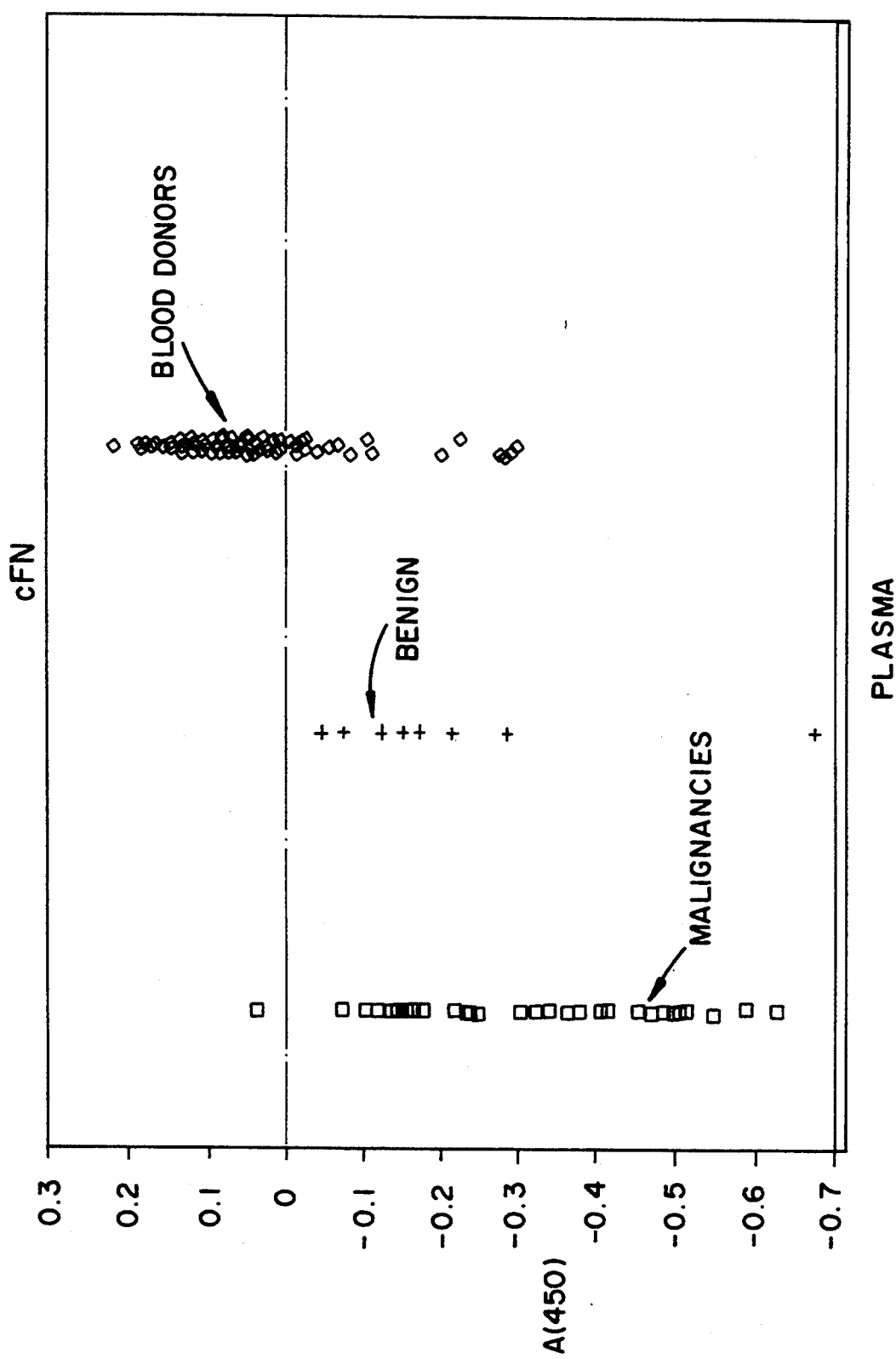
FIG. 2 shows cellular fibronectin content of sera and plasma from healthy blood donors and patients having malignant tumors or benign conditions according to Example 2.

In the enzyme immunoassay procedure used, cellular fibronectin antigen present in the sample competes with the cellular fibronectin bound to the microtitre plates for enzyme-labelled antibody. The amount of enzyme activity associated with the coated wells decreases with increasing amounts of cellular fibronectin in the sample (FIG. 2).

ELISA assays

In competitive ELISA assays sera and citrated plasma were used as samples. The assays were performed by conventional methods. It has been shown previously that levels of total fibronectin tend to be lower in serum than in plasma. This is supposedly due to the binding of fibronectin to fibrin (Engvall et al., 1978, J. Exp. Med., 147:1584). In our experiments, serum samples were also found to have lower concentrations of cellular fibronectin than the corresponding plasma. Table 1 shows an example of the results obtained with competitive ELISA of cellular fibronectin in normal human plasma, normal human serum, and in plasma and serum of patients with various malignancies. These results confirm the results given in the FIG. 2, i.e. malignant conditions show increased fibronectin amounts.

In the ELISA assay, absorbancies were measured at 450 nm.

TABLE 1

| Example of the results obtained with competitive ELISA. (Absorbencies at 450 nm) | | |
|---|---|---|
| cFN in | plasma | serum |
| Normal | 1.337 | 1.586 |
| 1) | 0.702 | 1.208 |
| 2) | 0.233 | 0.600 |
| 3) | 0.431 | 0.591 |
| 4) | 0.729 | 1.189 |
| 5) | 0.337 | 1.125 |
| 6) | 0.430 | 0.733 |
| 7) | 0.430 | 1.152 |

Legends:
cFN = cellular fibrnectin
1) pancreatic cancer, 2) adenocarcinoma, 3) stomach cancer, 4) colon carcinoma, 5) renal cancer, 6) duodenal wall sarcoma, 7) intenstinal cancer.

Immunoblotting of FNs by the monoclonal antibodies

Figure 3A:
FIGS. 3a and 3b show immunoblotting assay of cellular fibronectin (3a) and total fibronectin (3b) in serum and plasma from normal blood donors and from cancer patients according to Example 2.
Figure 3B:
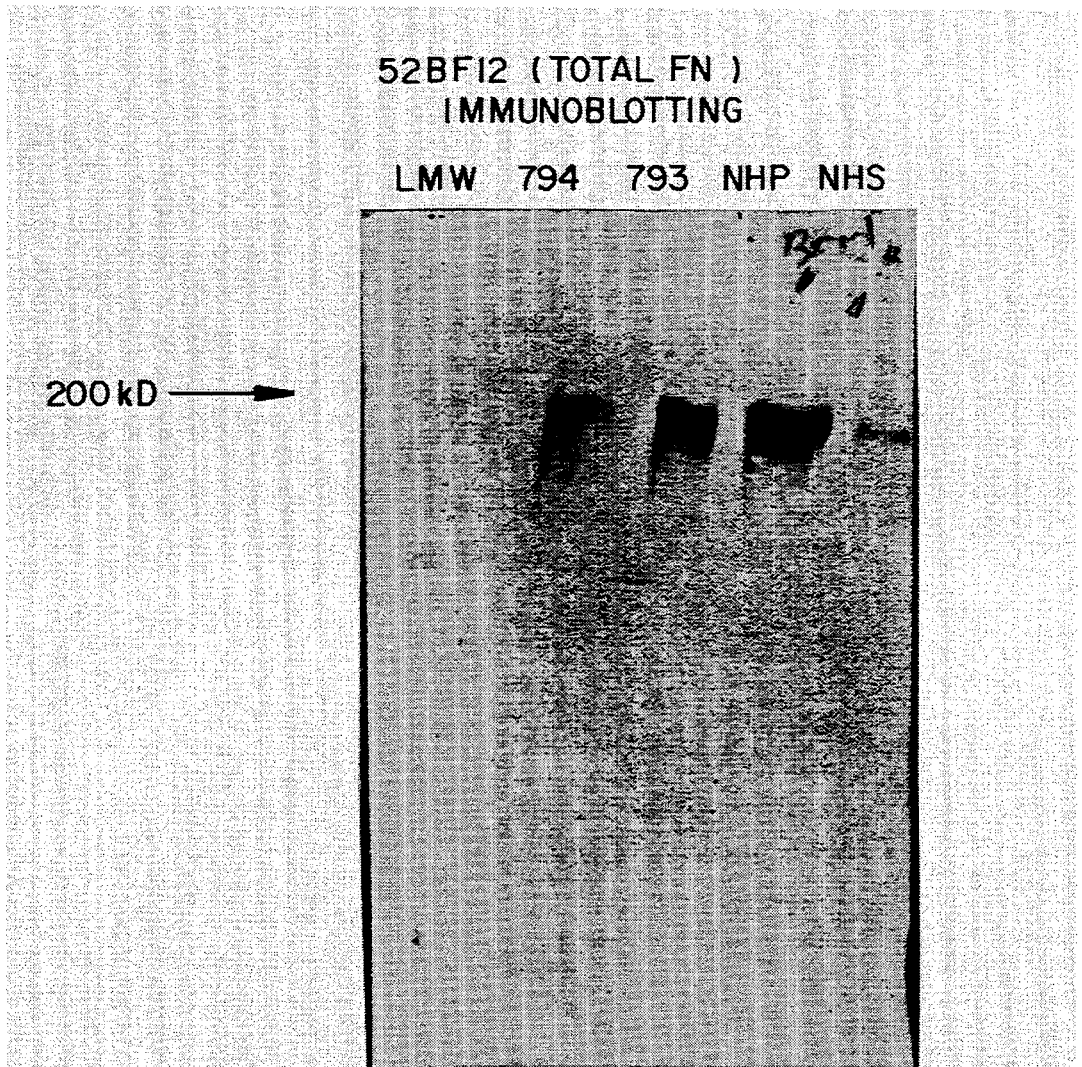

Fibronectins isolated from equal amounts of plasma and sera of a cancer patient and blood donors were immunoblotted for total and EDA-fibronectin by the 52BF12 (BF) and 52DH1 (DH) monoclonal antibodies, respectively (FIG. 3). The BF antibody reacted with all plasma and serum samples at the position of about MW 220 000, reacting most strongly with normal human plasma. Immunoblotting with DH1 revealed the presence of a slightly slower migrating EDA-containing subunits at the top of the bulk protein. The intensity of this band visually correlated to the changed levels of EDA-fibronectin measured by ELISA, also showing the higher overall concentrations of fibronectin in plasma samples. Consistent with the ELISA results, the Western transfer examination of cellular fibronectin revealed an increased concentration of EDA-fibronectin in the plasma and sera of cancer patients compared to normal blood donors.

We claim:

1. A method for screening for the presence of a malignant tumor in a patient, comprising:
   a) determining the concentration of at least one of extra domain A-containing cellular fibronectin and its extra domain A sequence in a sample of plasma or serum from the patient by an immunoreaction with an antibody that specifically binds to the extra domain A sequence indicative of said malignant tumor; and
   b) comparing the determined concentration with an average concentration of extra domain A-containing cellular fibronectin or its extra domain A sequence in healthy patients, at least a twofold increase of extra domain A-containing cellular fibronectin or its extra domain A sequence in said sample of said patient, as compared to healthy blood donors, indicating the possible presence of said malignant tumor.

2. A method as claimed in claim 1, wherein the tumor is a carcinoma.

3. A method as claimed in claim 2, wherein the carcinoma is a colon carcinoma.

4. A method as claimed in claim 1, wherein the sample is a serum sample.

* * * * *

UNITED STATES PATENT AND TRADEMARK OFFICE
CERTIFICATE OF CORRECTION

PATENT NO. : 5,420,012
DATED : May 30, 1995
INVENTOR(S) : Partanen et al.

It is certified that error appears in the above-indentified patent and that said Letters Patent is hereby corrected as shown below:

Column 3, line 57, delete "150" and substitute therefor --1:50--.

Column 4, line 11, delete "AMA" and substitute therefor --autoimmune--;

line 13, after "antibodies" insert --, AMA--.

Signed and Sealed this

Ninth Day of January, 1996

Attest:

BRUCE LEHMAN

*Attesting Officer*    *Commissioner of Patents and Trademarks*